(12) United States Patent
Krumme et al.

(10) Patent No.: US 8,129,865 B2
(45) Date of Patent: Mar. 6, 2012

(54) INDUCTIVE SYSTEMS FOR NON-CONTACT TRANSMISSION OF ELECTRICAL ENERGY

(75) Inventors: Nils Krumme, Feldafing (DE); Georg Lohr, Eichenau (DE); Herbert Weithmann, Munich (DE); Michael Bley, Landsberied/Babenried (DE)

(73) Assignee: Schleifring und Apparatebau GmbH, Fuerstenfeldbruck (DE)

( * ) Notice: Subject to any disclaimer, the term of this patent is extended or adjusted under 35 U.S.C. 154(b) by 279 days.

(21) Appl. No.: 12/435,604

(22) Filed: May 5, 2009

(65) Prior Publication Data
US 2009/0276199 A1    Nov. 5, 2009

Related U.S. Application Data

(63) Continuation of application No. PCT/EP2007/009631, filed on Nov. 7, 2007.

(51) Int. Cl.
*H01F 27/42* (2006.01)
*H01F 37/00* (2006.01)
*H01F 38/00* (2006.01)

(52) U.S. Cl. .................. 307/104; 378/4; 378/15
(58) Field of Classification Search .................. 307/104
See application file for complete search history.

(56) References Cited

U.S. PATENT DOCUMENTS

| | | | |
|---|---|---|---|
| 4,982,415 A * | 1/1991 | Shibata et al. | 378/15 |
| 5,892,411 A | 4/1999 | Schwan et al. | |
| 5,978,438 A * | 11/1999 | Resnick et al. | 378/4 |
| 6,351,626 B1 * | 2/2002 | Lohr | 455/41.1 |
| 7,899,150 B2 | 3/2011 | Beyerlein et al. | |
| 2003/0075670 A1 * | 4/2003 | Tuominen | 250/205 |
| 2004/0218406 A1 | 11/2004 | Jang et al. | |
| 2005/0045720 A1 * | 3/2005 | Fruhauf | 235/440 |
| 2005/0046584 A1 * | 3/2005 | Breed | 340/825.72 |
| 2005/0054306 A1 | 3/2005 | Schilling et al. | |

FOREIGN PATENT DOCUMENTS

| | | |
|---|---|---|
| DE | 29580172 | 7/1997 |
| DE | 19962068 | 7/2001 |
| DE | 10241581 | 3/2004 |
| DE | 102004051170 | 5/2006 |
| EP | 0953225 | 10/2006 |
| JP | 2004-248365 | 9/2004 |
| JP | 2006-217731 | 8/2006 |
| WO | 98/32217 | 7/1998 |
| WO | 03/085797 | 10/2003 |

OTHER PUBLICATIONS

WO Pub 2005064625 to Krumme, english abstract, Jul. 14, 2005.*

* cited by examiner

*Primary Examiner* — Rexford Barnie
*Assistant Examiner* — Justen Fauth
(74) *Attorney, Agent, or Firm* — Kevin L. Daffer; Daffer McDaniel, LLP

(57) ABSTRACT

An inductive rotary joint for non-contact transmission of electrical energy between a stationary part and a rotating part of the rotary joint comprises a power generator for generating an alternating voltage or an alternating current, which feeds a load by means of a rotatable power transmitter. An electrical parameter on the primary side of the power transmitter is determined with a measurement means, and from this, the condition of another electrical parameter at the load is approximated by means of a functional unit. Regulation of the power generator is effected with this approximated value.

20 Claims, 2 Drawing Sheets

INDUCTIVE SYSTEMS FOR NON-CONTACT TRANSMISSION OF ELECTRICAL ENERGY

PRIORITY CLAIM

The present application is a continuation of pending International Patent Application No. PCT/EP2007/009631 filed on Nov. 7, 2007, which designates the United States and claims priority to German Patent Application No. 102006052685.6 filed on Nov. 7, 2006 (now abandoned).

BACKGROUND OF THE INVENTION

1. Field of the Invention

The invention relates to an inductive rotary joint for transmitting electrical power between two units that are rotatable relative to each other, in particular for use in computer tomographs.

2. Description of the Related Art

Non-contacting inductive rotary joints are an advantageous substitute for the known mechanical slip-rings for transmission of electrical energy. In inductive transmission technology a coupling between rotatable units is effected with magnetic fields without contact. This has an advantage over mechanical slip-rings in that torque, wear, and thus, also an outlay of servicing are minimized. Furthermore, the surroundings of the rotary joints are not polluted by carbon dust.

Inductive rotary joints have at least one winding on each of the rotatable units. Furthermore, an iron core or ferrite core for controlling the magnetic field may be provided on the rotor, on the stator, or also on both parts. An alternating current signal is fed into a winding of one of the parts and tapped-off from another winding on the other part, and is supplied to a load. A rotary joint of this kind is disclosed, for example, in German Patent No. 29580172.

With a conductively coupled slip-ring it is possible, for example, for a constant voltage from a voltage source to be fed into the slip-ring and to be tapped off from a load on the other side in a simple manner. Because of the conductive connection of low ohmic resistance through the slip-ring, the output voltage will correspond to the input voltage, except for minor deviations. Owing to the low resistance of the slip-ring, a slight and usually negligible voltage drop depending on the load current is obtained.

With inductively coupled rotary joints, an equivalent circuit diagram of the transmission device will include a stray inductance as a series inductance between the input side and the load side. This stray inductance depends on the intrinsic inductance of the joint and, in particular, on the coupling factor. Especially with inductive rotary joints of large dimensions, it is often possible to obtain only a small coupling factor which, in addition, frequently fluctuates with the positions of the rotatable units relative to each other. Thus, for example, the coupling factor decreases with increase of an air-gap between the iron cores that are rotatable relative to each other. The stray inductance then increases accordingly. Now, in order to transmit higher power via the rotary joint despite this stray inductance, the stray inductance is used in suitable circuits like a discrete inductance. Its use would be, for example, as a storage inductance, or also as a resonance inductance. In the case of a resonance inductance, the inductance can be supplemented, for example, with a series capacitance to form a series resonance circuit, or with a parallel capacitance to form a parallel resonance circuit. Of course, more complex filter structures also may be obtained.

A rotary transmission device having resonance circuits is disclosed, for example, in European Patent No. 0953225.

With circuits of this kind, it is a problem that a measurement means is always needed on the output side of the rotary joint. In most known resonance circuits having a series inductance, at least one, and usually also several of the output parameters, such as current, voltage, or power vary with a change of the load impedance. This is not a problem in the case of a contacting slip-ring, as the load is preferably fed at a constant voltage, which can be transmitted via the slip-ring without difficulty and is substantially independent of load.

However, in the case of a typical non-contacting rotary joint having a series inductance, the output voltage, output current, and output power change with a change of the load impedance. Furthermore, the series inductance is changed owing to mechanical tolerances during the movement of the rotatable parts relative to each other. In order to achieve a uniform supply to the output side, and to prevent a destruction of the connected components, it is necessary to regulate at least one of the electrical characteristics on the output side. For low power, a separate regulator such as a voltage regulator that is constructed to be a series regulator, or also a switching controller may be used. For higher power, at least one sensor for one of these electrical parameters should be provided on the output side. This sensor determines the magnitude of the electrical parameter(s), and signals the magnitude to the alternating signal source on the input side. Now an electrical parameter such as, for example, the current, voltage or frequency on the input side can be regulated with a control amplifier so that a supply is ensured, for example, at constant voltage. A technology of this kind is used in conventional switching power supplies.

With rotary joints, however, there is the problem that information from a sensor must be transmitted from the output side to the input side, i.e., between two units that are rotatable relative to each other. This requires a further rotary joint operating in an opposite transmission direction from that of the inductive power transmitter. A solution to this problem is disclosed, for example, in German Patent No. DE 29580172 U1 in the form of a capacitive coupling element. However, often no mechanical construction space is available for a capacitive coupling element of this kind, or else a coupling element of this kind is needed for data transmission for other data such as measurement data, for example, and therefore cannot be used for regulating purposes.

The problems described above increase with increase of size of the rotary joint. Thus, with compact units having diameters of a few centimeters it is still possible to use precise bearings with tolerances below 0.1 mm. With this, it is possible to achieve, for example, a precise air-gap of 0.2 mm, and a fluctuation in a range of 0.2 mm to 0.3 mm. With large units having diameters larger than 1 meter, as used for example in computer tomographs, the tolerances are already in a range of a few millimeters, and are partly greater than 5 mm. Thus, in a case like this the air-gap would vary between 1 and 6 mm, depending on position and operating conditions. This leads to a substantially larger stray inductance, which fluctuates substantially more strongly.

SUMMARY OF THE INVENTION

The following description of various embodiments of inductive rotary joints is not to be construed in any way as limiting the subject matter of the appended claims.

An object of the disclosure provided herein is to design a rotary joint for non-contacting inductive transmission of electrical power, so that a feedback from an output side sensor for at least one electrical parameter to an alternating current source on an input side is no longer needed.

According to one embodiment, an inductive rotary joint for non-contacting transmission of electrical energy between a stationary and a rotating part comprises: a power generator for generating an alternating voltage or an alternating current; an inductive power transmitter having a primary side and a secondary side, in which the primary side is fed by the power generator and the secondary side serves to feed a load; a measurement means for determining at least one electrical parameter such as a voltage, a current, a phase angle of electrical energy fed by the power generator into the primary side of the power transmitter; and a functional unit for controlling the power generator with the aid of the at least one electrical parameter so that at least one other electrical parameter on the load, such as a voltage, a current, a phase angle, is maintained approximately constant. According to one embodiment, the functional unit comprises a model for simulating a transmission function, i.e., a relationship between the electrical parameter or parameters on the load and the electrical parameter or parameters on the primary side.

BRIEF DESCRIPTION OF THE DRAWINGS

In the following, the invention will be described by way of example, without limitation of the general inventive concept, on an example of embodiment and with reference to the drawings.

Figure 1:
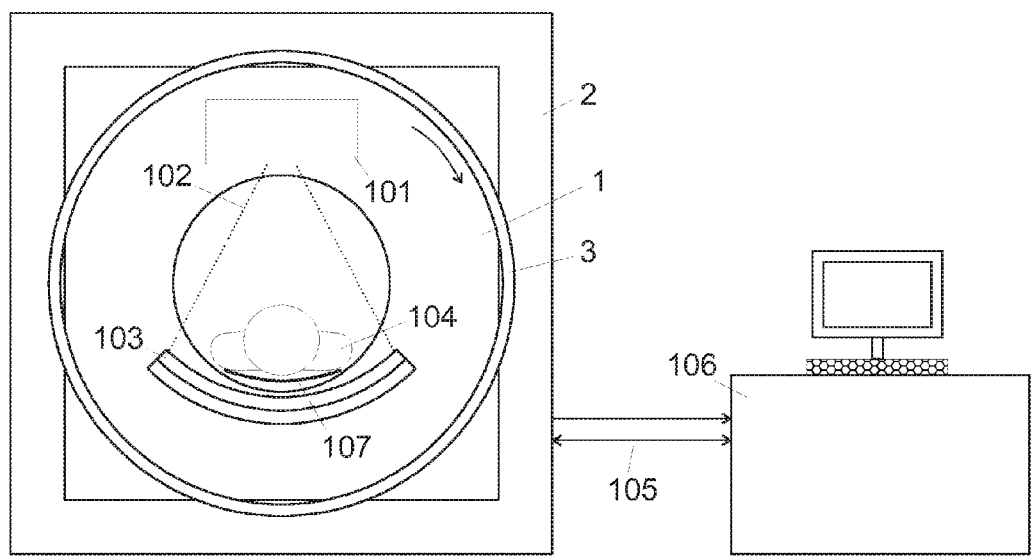
FIG. 1 schematically shows an embodiment of a computer tomograph (CT) scanner.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

FIG. 1 shows an embodiment of a computer tomograph (CT) scanner comprising two mechanical main parts. A stationary part 2 serves as a base and support for the entire instrument, within which a rotating part 1 revolves. A patient 104 is positioned on a berth 107 in an opening of the rotating part. An X-ray tube 101 and an oppositely positioned detector 103 are provided for scanning the patient by means of X-rays 102. The X-ray tube 101 and the detector 103 are disposed to be rotatable on the rotating part 1. A rotary joint 3 serves to provide an electrical connection between the rotating part 1 and the stationary part 2 of the CT machine. In this, high electrical power for feeding the X-ray tube 101 is transmitted in a direction towards the rotating part 1, and raw data of an image obtained by the detector 103 are simultaneously transmitted in an opposite direction. A communication of control information in both directions is provided in parallel with this. An evaluation and control unit 106 serves for operating the computer tomograph, and also for displaying the generated images. Communication with the computer tomograph is effected via a bidirectional link 105.

Figure 2:
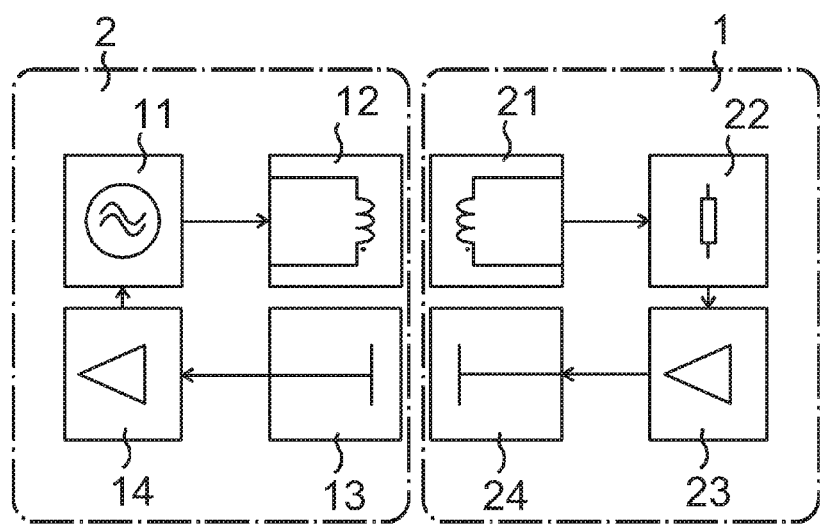
FIG. 2 schematically shows an embodiment of a non-contacting rotary joint according to prior art.

FIG. 2 is a schematical representation of a non-contacting rotary joint according to prior art. Energy is transmitted from a stationary part 2 to a rotating part 1 of the non-contacting rotary joint. A power generator 11 for feeding a primary side 12 of a power transmitter with an alternating current signal or a pulsating direct current signal is located in the stationary part 2. The power generator is preferably a switching amplifier or a switching stage. The power generator is typically provided with a half-bridge or full bridge circuit, preferably having Insulated Gate Bipolar Transistors (IGBTs) or Metal Oxide Semiconductor Field Effect Transistors (MOSFETs). Supply of this stage is effected preferably from an alternating-current voltage line, for example, via a rectifier, but preferably via a power-factor correction circuit.

For feeding the load 22, the primary side 12 of the power transmitter is magnetically coupled with the secondary side 21 of the power transmitter. A measuring amplifier 23 determines particular measurement parameters, which characterize the load 22 or an operating state of the load. A measurement parameter of this kind may be, for example, a voltage applied to the load, or a current flowing through the load. Typically, a load 22 is supplied with direct current. For this reason, a rectifier (not shown) with optional smoothing and optional control circuitry is provided between the load 22 and the secondary side 21 of the power transmitter. In this case, the measurement parameter would be a direct current voltage on the load 22 or a direct current through the load 22.

The output signal from the measuring amplifier 23 is sent by means of a signal transmitter having a primary side 24 and a secondary side 13 to a control amplifier 14 for controlling the power generator 11. The control amplifier 14 compares the input parameter (i.e., the measurement parameter measured by means of the measuring amplifier 23) with a desired value, and provides a differential signal to the power generator 11. With this arrangement, a closed regulating loop is obtained which maintains a measurement parameter representing the load, such as the voltage on the load or the current through the load, constant. Of course, instead of the previously described measurement parameter, several measurement parameters can be used for regulation. Accordingly, several signal transmitters will be needed. Alternatively, a signal transmitter can be operated according to a multiplex method. A disadvantage of this arrangement is that an additional signal transmission device is needed.

Figure 3:
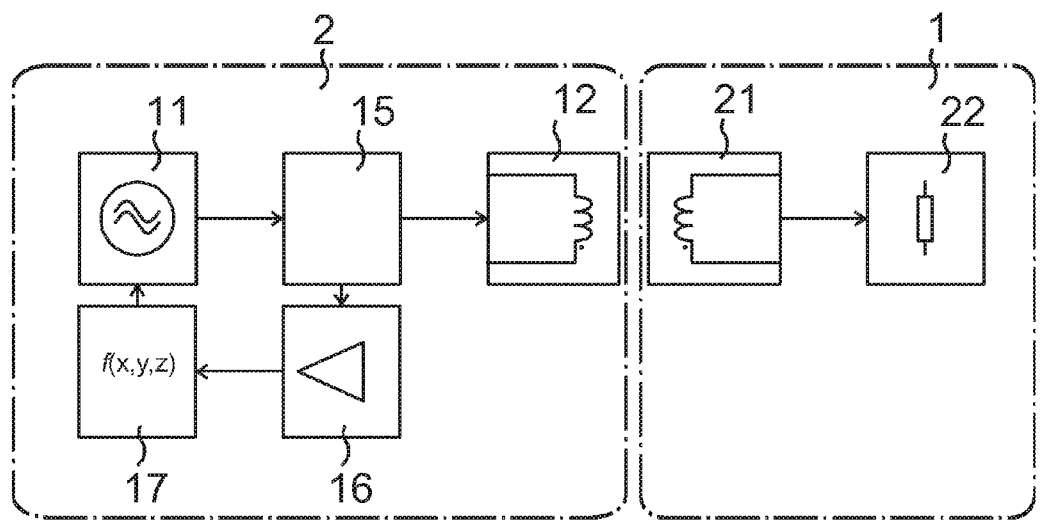
FIG. 3 schematically shows a preferred embodiment of a non-contacting rotary joint.

FIG. 3 is a schematic representation of a rotary joint in accordance with a preferred embodiment of the invention. Like the previous embodiment, a power generator 11 is included on the stationary side 2 for generating a high-frequency alternating current signal or a pulsating direct current signal, which is fed into the primary side 12 of the power transmitter. On the rotating side 1, a load 22 is fed through the secondary side 21 of the power transmitter.

Unlike the previous embodiment, a measurement means 15 is provided on the stationary side 2 between the power generator 11 and the primary side 12 of the power transmitter. This measurement means determines at least one, and preferably a plurality of electrical parameters of the signal generated by power generator 11. For example, the measurement means 15 may determine one or more of following electrical parameters: the current in the primary side 12 of the power transmitter, the voltage on the primary side 12 of the power transmitter, a phase angle, or another parameter. The one or plurality of electrical parameters determined by the measurement means 15 are amplified via a measuring amplifier 16 and are passed to a functional unit 17, both of which are included on the stationary side 2 of the rotary joint.

The functional unit 17 provides a control signal to the power generator 11 for controlling the power generator in dependence on the measurement parameters. For this, the functional unit 17 possesses a function model of the transmission function [ƒ(x,y,z)] of the load transformed onto the primary side 12 of the power generator. This function model derives the transmission function of the load in dependence on various measured parameters. With the function model, for example, the voltage applied to the load could be estimated in dependence on the voltage or current values measured by the measurement means 15. In addition or alternatively, the current flowing into the load, or the power taken up by the load, could be estimated by the function model.

The rotary joint shown in FIG. 3 comprises a power generator 11 for generating an alternating voltage or an alternating current, or alternatively, a pulsating direct current. Furthermore, a power transmitter is provided, which comprises a primary side 12 and a secondary side 21. The primary side 12 is fed from the power generator 11, whilst the secondary side 21 serves to feed a load 22. The primary side 12 and the secondary side 21 are disposed to be rotatable relative to each other. Thus, the primary side 12 is located, for example, on a stationary part 2, and the secondary side 21 is located on a rotating or rotatable part 1. Furthermore, a measurement means 15 is provided for determining at least one electrical parameter on the primary side 12 of the power transmitter. A parameter of this kind may be, for example, a voltage such as the voltage on the primary side 12, a current such as the current into the primary side 12, a power such as the power fed into the primary side 12, or also a phase angle such as the phase angle between current and voltage on the primary side 12. Further electrical parameters such as, for example, the spectral composition may be also determined by the measurement means 15.

As shown in FIG. 3, a functional unit 17 is provided on the stationary side for evaluating the at least one electrical parameter obtained from the measurement means 15 and generating from this a control signal for the power generator 11. The power generator 11 is controlled by this control signal so that at least one further electrical parameter on the load 22 is approximately constant. A further electrical parameter of this kind can be, for example, a voltage such as the voltage at the load 22, a current such as the current into the load 22, a power such as the power transferred into the load 22, or also a phase angle such as the phase angle between current and voltage at the load 22. Now, in order to maintain this further electrical parameter approximately constant, the functional unit 17 is provided with a model for simulating the transmission function, ƒ(x,y,z), i.e., the relationship between the at least one electrical parameter at the load 22 and the at least one parameter on the primary side 12.

The functional unit 17 is provided with all components necessary for obtaining a closed loop control circuit. This typically means that a differential amplifier (not shown) is also provided for comparing the output signal of the model used for simulating the transmission function with a given desired value, and then passing the amplified difference to the power generator 11. The differential amplifier may be a proportional, proportional/integral, or also proportional/integral/differential amplifier. However, such an amplifier may not be included in all embodiments. In an especially simple case, only a control signal (for example, for controlling power emission) is sent by the functional unit 17 to the power generator 11. However, greater flexibility can be achieved if several signals such as, for example, control signals for power emission and frequency are sent from the functional unit 17 to the power generator 11. The use of multiple control signals has the disadvantage of increasing the complexity of the entire arrangement and particularly the functional unit 17.

In some embodiments, the power generator 11, measurement means 15, and the optional measuring amplifier 16 are functional elements which, for example, may be incorporated in a component group. In some embodiments, an analog and/or digital filtering of the measurement parameters may be provided instead of, or in addition to, the measuring amplifier 16.

Advantageously, the functional model [ƒ(x,y,z)] is a characteristic function or a family of characteristic functions. This characteristic function or family of characteristic functions may be also multi-dimensional in accordance with the number of input parameters supplied by the measurement means 15, and the output parameters issued to the control amplifier 16.

In a particularly advantageous embodiment of the invention, the modeling of the characteristic function is effected on the basis of the results of a circuit simulation in which preferably the dependence of the voltage at the load 22 is represented as a function of the switching frequency of the power generator 11 and the current into the primary side 12 of the power generator.

In another advantageous embodiment of the invention, the model simulates the response of the arrangement on the basis of a simplified equivalent circuit diagram. For this, preferably only the resistive contributions of the switching transistors and conductors, the parasitic contributions of the windings and inductances, and also intentionally introduced resistances are taken into account. Furthermore, use is made of the inductive equivalent circuit diagram of the power transmitter with its primary side 12 and its secondary side 21. Finally, the capacity of any present resonance capacitors is taken into account.

In another embodiment, the modeling is effected on the basis of at least one transmission characteristic function obtained by measurement. This represents, in an advantageous manner, the dependence of the output voltage on the switching frequency of the power generator 11, and on the current fed into the primary side 12 of the power transmitter, and also on the power taken up by the load 22 or on the resistance of the load 22.

In another embodiment, the model approximates at least one range of the transmission function of the arrangement as being a linear function, by a straight line. This is particularly expedient when the load has a known and preferably limited dynamic range. If a minimum and a maximum load resistance are known, then the characteristic function can be usually approximated within this range preferably by a straight line, and optimized.

Another embodiment provides a model in the form of a simulation of the transmission function with analog passive components. These could be components having suitable electrical parameters, located in a power path between the power generator 11 and the load 22, wherein their stability under load can be considerably smaller.

Another embodiment provides for the model to approximate at least a range of the transmission function by means of a resistance- and diode-network. A network of this kind can be provided, for example, in the circuitry of an operational amplifier. As an alternative to this, an approximation of the transmission function by means of a logarithmic amplifier is also possible.

Another embodiment provides for the model to also take into account at least one mechanical parameter, such as the distance between the rotating part 1 and the stationary part 2, the size of the air-gap between the primary side 12 of the power transmitter and the secondary side 21 of the power transmitter, or the angular position between the rotating part 1 and the stationary part 2. In the latter case, the transmission function becomes position-dependent as a result of a summation of various mechanical parameters and tolerances. The inclusion of a mechanical parameter is particularly expedient, because there is a direct relationship between the stray inductance and the air-gap, i.e., the distance between the windings or the core of the primary side 12 of the power transmitter and the secondary side 21 of the power transmitter.

Measurement of a mechanical parameter of this kind is preferably obtained with a path sensor or a position encoder (not shown), but also can be performed, for example, in the case of an angular position, by measurement of time of movement from a point of reference. Similarly, a measurement by evaluation of the capacitance between capacitor plates mounted on the rotating part 1 and the stationary part 2, or the capacitance between the primary side 12 and the secondary side 21 of the power transmitter is possible. Alternatively, a mechanical parameter of this kind can be signaled by a higher-ranking control unit (not shown), which controls the complete system status of a facility, such as a computer tomography (CT) scanner. Furthermore, it is of advantage for the functional unit to be provided with a digital computer, preferably a digital signal processor.

In one embodiment, the model can be stored as a mathematical model in the functional unit 17, so that the transmission function is calculated in dependence on the input parameters at each time of operation.

In another embodiment, the model can be stored in the form of a table, with or without interpolation, in a storage device such as, for example, a Read Only Memory (ROM).

Another advantageous embodiment provides for the functional unit 17 to have means for adaptive measurement or adaptive learning of the model parameters. Thus, for example, the exact parameters of the model under specific operating conditions can be determined during or before the device is put into operation. Thus, for example, as a preliminary measure a cable used for measurement, or also a digital data path, could be connected to the functional unit 17 for measuring the voltage at the load 22, so that the functional unit can determine the actual conditions at the load for various conditions of the power generator 11. Furthermore, various different loads could be connected instead of the load 22 to determine the characteristic function. This adaptive measurement can be effected, for example, without performing a rotational movement by bridging the rotary joint with a cable. Alternatively, a restricted rotational movement, for example through 360°, can also be performed with a cable to determine the angular dependence. As an auxiliary measure, another rotary joint also could be fitted to obtain results for a plurality of revolutions or for operation during rotation.

It is of particular advantage when certain operating conditions, such as short circuits or idle running, can be used for determining the parameters. Operating conditions of this kind result, for example, during start-up of the circuit; however, they also can be brought about intentionally by means of switches (idle operation, short circuits). Thus, a low-ohm, short-circuit-like operating condition occurs when filter capacitors connected to follow a rectifier for the supply voltage to the load 22 are not yet charged. A high-ohm, operating condition could arise when the load 22 is connected into the circuit only after a certain time delay, or only as from a given input voltage. Further parameters can be determined from these conditions. The causes for the kinds of special operating conditions can also be affected intentionally to maintain these operating conditions for a longer period of time, which is sufficient for measurements. Thus, for example, the filter capacitors could be enlarged, or also a time delay prolonged.

The reliability can be increased with further additional protective circuits. Thus, for example, a voltage such as the voltage on the load 22, or a voltage on the primary side 12 of the power transmitter can be monitored. Furthermore, an estimate of the value of the voltage at the load 22 is possible with the aid of the functional unit 17. As an alternative to this, a signal transmitter 24, 13 could be used for monitoring the voltage. When a limiting value is exceeded, in the case of the power transmitter being connected as a series resonance circuit, a short circuit of the secondary side 21 of the power transmission device can occur. Similarly, in the case of the power transmitter being connected as a parallel resonance circuit, the secondary side 21 of the power transmitter can be separated from the load 22. In this case, it is particularly advantageous for the load 22 to remain completely separated from the secondary side 21 of the power transmitter until the capacitances in the arrangement have been sufficiently discharged.

For illustration of the principle of operation, explanation is provided above in reference to a transmission from a stationary part (stator) to a rotating part (rotor) via a rotary joint. Similarly, a transmission between a rotating part and a stationary part is also possible, because this is only a question of reference to location. In addition to inductive transmission between rotatable parts, an inductive transmission between parts that are movable linearly relative to each other is also possible. The embodiments described herein relate to the inductive coupling between parts that are movable relative to each other in a general manner, and is independent of the kind of movement of these parts relative to each other. Thus, the disclosed embodiments are usable not only with rotary joints but also, for example, with linear transmission devices.

A computer tomograph in accordance with the invention comprises at least one inductive rotary joint as described above.

It will be appreciated to those skilled in the art having the benefit of this disclosure that this invention is believed to provide inductive rotary joint for non-contacting inductive transmission of electrical power. More specifically, the invention provides an inductive rotary joint, which avoids a feedback from an output side sensor for at least one electrical parameter to an alternating current source on an input side. Further modifications and alternative embodiments of various aspects of the invention will be apparent to those skilled in the art in view of this description. It is intended, therefore, that the following claims be interpreted to embrace all such modifications and changes and, accordingly, the specification and drawings are to be regarded in an illustrative rather than a restrictive sense.

What is claimed is:

1. An inductive rotary joint for non-contact transmission of electrical energy between a stationary part and a rotating part of the rotary joint, comprising:
   a power generator disposed on the stationary part for generating an alternating voltage or an alternating current;
   an inductive power transmitter comprising a primary side disposed on the stationary part and a secondary side disposed on the rotating part, in which the primary side is fed by the power generator and the secondary side feeds a load;
   a measurement means disposed on the stationary part and operationally coupled between the power generator and the primary side of the inductive power transmitter for determining at least one electrical parameter selected from a group comprising: a voltage, a current, and a phase angle of electrical energy fed by the power generator into the primary side of the power transmitter; and
   a unit disposed on the stationary part and operationally coupled between the measurement means and the power generator for controlling the power generator with the aid of the at least one measured electrical parameter, so that at least one other electrical parameter on the load is maintained approximately constant, wherein the at least one other electrical parameter is selected from a group comprising a voltage, a current, and a phase angle of the electrical energy fed onto the load, and wherein the unit comprises a computer readable medium with a model for simulating a relationship between the at least one other electrical parameter on the load and the at least one electrical parameter on the primary side of the power transmitter.

2. The rotary joint according to claim 1, wherein the model is a characteristic function or a family of characteristic functions.

3. The rotary joint according to claim 2, wherein the characteristic function simulates a circuit in which dependence of voltage on the load is a function of a switching frequency of the power generator and current into the primary side of the power transmitter.

4. The rotary joint according to claim 2, further comprising a control amplifier disposed within the stationary part and operationally coupled between the measurement means and the unit, wherein characteristic function or family of characteristic functions are multi-dimensional in accordance with a number of input parameters supplied by the measurement means and output parameters sent to the control amplifier.

5. The rotary joint according to claim 1, wherein the model simulates a response of the rotary joint under an assumption of a simplified equivalent circuit diagram.

6. The rotary joint according to claim 1, wherein the model is based on at least one transmission characteristic function obtained by measurement.

7. The rotary joint according to claim 6, wherein the model approximates at least one range of the transmission characteristic function as being a linear function.

8. The rotary joint according to claim 6, wherein the model comprises a simulation of the transmission characteristic function with analog passive constructional components.

9. The rotary joint according to claim 6 wherein the model approximates at least one range of the transmission characteristic function by means of a resistance- and diode-network.

10. The rotary joint according to claim 6, wherein the model approximates at least one range of the transmission characteristic function by means of a logarithmic amplifier.

11. The rotary joint according to claim 1, wherein the model also takes into account at least one mechanical parameter selected from a group comprising: a distance between the rotating part and the stationary part, a size of an air-gap between the primary side of the power transmitter and the secondary side of the power transmitter, and an angular position between the rotating part and the stationary part.

12. The rotary joint according to claim 1, wherein the unit comprises a digital computer having a digital signal processor.

13. The rotary joint according to claim 1, wherein the model is a mathematical model.

14. The rotary joint according to claim 1, wherein the model is a data table.

15. The rotary joint according to claim 1, wherein the unit comprises means for adaptive measurement or adaptive learning of model parameters.

16. A computer tomograph comprising:
a rotating part for accommodating an X-ray tube and a detector:
a stationary part for rotatably supporting the rotating part;
a power generator disposed on the stationary part forgenerating an alternating voltage or an alternating current;
an inductive power transmitter comprising a primary side disposed on the stationary part and a secondary side disposed on the rotating part, in which the primary side is fed by the power generator and the secondary side feeds the X-ray tube;
a measurement means disposed on the stationary part and operationally coupled between the power generator and the primary side of the inductive power transmitter for determining at least one electrical parameter selected from a group comprising: a voltage, a current, and a phase angle of electrical energy fed by the power generator into the primary side of the power transmitter; and
a unit disposed on the stationary part and operationally coupled between the measurement means and the power generator for controlling the power generator with the aid of the at least one measured electrical parameter, so that at least one other electrical parameter on the load is maintained approximately constant, wherein the at least one other electrical parameter is selected from a group comprising a voltage, a current, and a phase angle of the electrical energy fed onto the load, and wherein the unit comprises a computer readable medium with a model for simulating a relationship between the at least one other electrical parameter on the load and the at least one electrical parameter on the primary side of the power transmitter.

17. The computer tomograph according to claim 16, wherein the model is a mathematical function.

18. A system, comprising:
a first part comprising a power generator for generating an alternating voltage or an alternating current;
a second part spaced apart from the first part, wherein at least one of the first and second parts is moveable during operation of the system;
an inductive power transmitter comprising a primary side disposed on the first part and a secondary side disposed on the second part, in which the primary side is fed by the power generator and the secondary side feeds a load;
a measurement means disposed on the first part and operationally coupled between the power generator and the primary side of the inductive power transmitter for determining at least one electrical parameter selected from a group comprising:
a voltage, a current, and a phase angle of electrical energy fed by the power generator into the primary side of the power transmitter; and
a unit disposed on the second part and operationally coupled between the measurement means and the power generator for controlling the power generator with the aid of the at least one measured electrical parameter, so that at least one other electrical parameter on the load is maintained approximately constant, wherein the at least one other electrical parameter.is selected from a group comprising a voltage, a current, and a phase angle of the electrical energy fed onto the load, and wherein the unit comprises a computer readable medium with a model for simulating a relationship between the at least one other electrical parameter on the load and the at least one electrical parameter on the primary side of the power transmitter.

19. The system according to claim 18, wherein the first part is a moveable part and the second part is a stationary part.

20. The system according to claim 19, wherein at least one of the first and second parts is configured to move linearly during operation of the system.

* * * * *